United States Patent [19]
Kershaw et al.

[11] Patent Number: 6,140,257
[45] Date of Patent: Oct. 31, 2000

[54] COMPOSITE FIBRES, WOUND DRESSINGS INCORPORATING SUCH FIBRES AND A METHOD FOR MAKING SAME

[75] Inventors: David Kershaw, Abergavenny; Peter M. J. Mahoney, Near Llanfyllin; Paul Hanmer, Buckley; David Pritchard, Cardiff, all of United Kingdom

[73] Assignee: Bristol-Myers Squibb Company, New York, N.Y.

[21] Appl. No.: 09/155,950

[22] PCT Filed: Apr. 11, 1997

[86] PCT No.: PCT/EP97/01880

§ 371 Date: Dec. 21, 1998

§ 102(e) Date: Dec. 21, 1998

[87] PCT Pub. No.: WO97/39170

PCT Pub. Date: Oct. 23, 1997

[30] Foreign Application Priority Data

Apr. 12, 1996 [GB] United Kingdom .................. 9607600
Sep. 6, 1996 [GB] United Kingdom .................. 9618658

[51] Int. Cl.$^7$ .............................. A61L 15/28; A61L 15/60
[52] U.S. Cl. .............................. 442/4; 442/304; 442/308; 442/310; 424/443; 424/445; 602/41; 604/304; 428/357; 264/176.1; 264/211
[58] Field of Search ................................ 442/4, 304, 308, 442/310; 424/445, 443; 602/41; 604/304; 428/357; 264/176.1, 211

Primary Examiner—Richard Weisberger
Attorney, Agent, or Firm—John M. Kilcoyne; Theodore R. Furman, Jr.

[57] ABSTRACT

An absorbent, composite fibre comprising a matrix of from 10% to less than 50% of water insoluble alginate having dispersed therein at least 40% of another polysaccharide.

20 Claims, No Drawings

COMPOSITE FIBRES, WOUND DRESSINGS INCORPORATING SUCH FIBRES AND A METHOD FOR MAKING SAME

The invention relates to composite fibres, particularly absorbent composite fibres for use in wound treatment, wound dressings incorporating such fibres and a method for making same.

Absorbent fibres for use in wound treatment are well known in the art. Examples include cellulose fibres, chemically modified cellulose fibres, pectin fibres, alginate fibres, chitosan fibres, hyaluronic acid fibres or other polysaccharide fibres or fibres derived from gums. In the treatment of wounds it is desirable to use fibres made from pectin or carboxymethyl cellulose but the known processes for making such fibres are complex and expensive and the resulting fibres not always viable. For instance it is known to make carboxymethyl cellulose fibres by chemically converting preformed cellulose fibres. It is also known that both pectin fibres and carboxymethyl cellulose fibres are difficult to spin.

It has been proposed in GB 2062652 A to make cellulose fibres comprising anionically modified polysaccharides by adding the polysaccharide to preformed viscose. Similarly in U.S. Pat. No. 4,063,558 there is described a method for making fibres of cellulose with alkali metal salts of alginic acid uniformly dispersed therein by adding a solution of sodium alginate to preformed viscose.

In WO 96/10106 there are described fibres which preferably comprise from 70 to 95% by weight of an alginate co-spun with from 5 to 30% by weight of at least one water soluble organic polymeric species (other than alginate).

We have now found that, it is possible to make a composite, absorbent fibre comprising a matrix of water insoluble alginate having another polysaccharide dispersed therein where the fibre comprises less than 50% by weight of the alginate, the fibre mitigating the disadvantages of the prior art fibres.

Accordingly the invention provides an absorbent, composite fibre comprising a matrix of at least 10% and less than 50% by weight of water insoluble alginate having dispersed therein at least 40% of another polysaccharide. Unless otherwise stated all percentages herein are by weight based on the weight of the fibre.

Whilst not wishing to be bound by theory it is believed that the water insoluble alginate effectively provides, as a matrix, a molecular backbone to the fibre that enables the other polysaccharides to be incorporated and results in a fibre that may be spun and otherwise processed. The use of water insoluble alginate for this purpose enables the fibres to be made without the need for complex and expensive processing and without the need to use preformed cellulose as a starting material. Preferred polysaccharides for addition to the alginate backbone are carboxymethyl cellulose and/or pectin.

Since it is believed that the fibres of the invention rely on the water insoluble alginate to provide integrity to the fibres it is truly surprising that it is possible to make viable fibres processable into products that comprise a minor proportion of insoluble alginate. One of the advantages of such fibres is that they may comprise a major proportion of polysaccharide other than alginate which generally makes them more absorbent than fibres which have insoluble alginates in a major proportion.

Preferably the fibres comprise, in addition to insoluble alginate, from 40% to 90% of another polysaccharide, more preferably from 60% to 85% and most preferably from 70% to 80% of another polysaccharide which is most preferably carboxymethyl cellulose or pectin or a mixture thereof. Polysaccharides suitable for use in fibres according the invention include carboxymethyl cellulose, carboxyethyl cellulose, other derivatives of cellulose, cellulose, pectin, hyaluronic acid and chitosan. Preferably the insoluble alginate is calcium alginate.

Preferably the fibres comprise from 10% to less than 50% by weight of the fibre of insoluble alginate, more preferably 10% to 49%, more preferably 15% to 40% and most preferably from 20% to 30% by weight of the fibre of water insoluble alginate. Preferably the insoluble alginate is calcium alginate.

A particularly preferred embodiment of the absorbent, composite fibres of the invention comprise a matrix of 20% to 30% of calcium alginate based on the weight of the fibre having dispersed therein from 55% to 60% of carboxymethyl cellulose and 15% to 20% of pectin based on the weight of the fibre.

Accordingly in another aspect the invention provides a method for making a composite, absorbent fibre comprising the following steps:

(i) adding sodium alginate and another polysaccharide to water to form a dope;
(ii) forcing the dope through a spinneret to form fibres;
(iii) treating the resulting fibres with a source of calcium ions to convert the alginate to calcium alginate and cross-link the alginate to the other polysaccharide;
(iv) drying the fibres.

The process enables composite fibres to be prepared which comprise large quantities of other polysaccharides and in particular, carboxymethyl cellulose, pectin or both. The fibres so produced are capable of being spun or otherwise mechanically processed. In addition the resulting fibres have a high tensile strength compared to alginate, carboxymethyl cellulose or pectin alone.

As used herein the term fibre means both relatively short, discrete, randomly oriented material (sometimes known as staple fibre) and yarns made therefrom (sometimes known as staple yarn) and relatively long, structured, continuous filament yarn. The fibres may have a staple length of 5 mm to 70 mm, more usually 20 mm to 50 mm, favourably 25 mm to 40 mm.

The fibres prepared according to the above described process may be dried using conventional methods, for example, using acetone or hot air drying.

Alginates are produced by a variety of micro-organisms and marine algae which are the normal commercial source. The alginates being natural materials show considerable variety but are characterised in being block copolymers, the individual monosaccharide units being arranged into groups as blocks of mannuronic (M) and guluronic (G) residues. In addition to the repeating blocks each polymer chain can contain a proportion of alternating M and G monosaccharide units. The alginate may be obtained from any convenient source, for example L. Hyperborea or Ascophyllum Nodosum or those described in EP-A-0721355 to Bristol-Myers Squibb Company which are particularly preferred.

In a further embodiment of the invention the absorbent, composite fibres are employed in the manufacture of wound dressings. Accordingly the invention provides a wound dressing comprising an absorbent, composite fibre comprising a matrix of between at least 10% and less than 50% of water insoluble alginate having dispersed therein at least 40% of another polysaccharide.

The wound dressings may be in the form of swabs, wound pads, wadding ribbons, sponges, nets and bandages and may be used as a primary or secondary dressing especially in the treatment of leg ulcers. The wound dressings according to the invention may benefit from an improved integrity over that of dressings made from alginate, pectin or carboxymethyl cellulose alone.

According to a further aspect of the invention there is provided a wound dressing comprising a mixture of discrete textile fibres and discrete absorbent, composite fibres said absorbent, composite fibres comprising a matrix of at least 10% of water insoluble alginate having dispersed therein at least 40% of another polysaccharide. Such a dressing may have the advantage that it is non-adherent to wound tissue while being absorbent and relatively inexpensive and the added advantage that it may be retained on the wound for longer than conventional cotton gauze. The absorbent, composite fibres according to the invention incorporated in the wound dressing become moist and slippery or gelatinous upon the uptake of wound exudate. This reduces the tendency for the textile fibres to adhere to the wound.

In general textile fibres absorb liquids by capillary action and are not hygroscopic. This means that their absorbencies as measured by the free swell absobancy test are low such as less than 1 gram of liquid per gram of fibre. Suitable textile fibres can be natural or synthetic depending on the end use of the dressing and method of manufacture. Suitable textile fibres are for instance described in PCT/GB95/00114. For example where the dressing is made from a non-woven mixture of discrete fibres the textile fibre is preferably one that can be fused at relatively low temperatures, for example polypropylene. The entire dressing can be heat fused to give a dressing with sufficient tensile strength that it may be removed intact from the wound even though saturated with exudate. This avoids the need for the painstaking removal from the wound of parts of a dressing that has lost its integrity on exposure to exudate.

Where the dressing is made from a woven mixture of discrete fibres the textile yarn can be polyester, polypropylene or polyamide or any other suitable support yarn. We have surprisingly found that it is possible to knit fibres of the invention in a knitting process where it is preferable for the textile yarn to form the pillar or chain stitches of the knit (the warp) and the composite fibre to form or be included in the the in-laid yarn of the knit. A particularly suitable knit of this type is a Raschel knit as described in Textile Science by Kathryn Hatch, West Publishing Company 1993. If composite fibres are included in both the pillar and the in-laid yarn then the pillar yarn tends to break and shed fibres. If composite fibres are included only in the in-laid yarn then this tendancy is overcome and quite high machine knitting speeds can be achieved and a dressing of better integrity is produced.

According to a further aspect the invention provides a wound dressing as claimed in claims 11 to 14 wherein the dressing is in the form of a warp knitted fabric comprising pillar yarn and in-laid yarn, the pillar yarn being substantially free of composite fibres.

Various optional ingredients can be included in the final composition of the fibres such as preservatives and small amounts of pharmacologically active ingredients. For example an antibiotic or antimicrobial agent such s metronidazole, silver sulphadiazine, neomycin or penicillin and antiseptic agent such as povidone iodine, iodine and antiinflammatory agent such as hydrocortisone or triamcinolone acteonide or a skin protective agent such as a zinc oxide can be included.

The invention is illustrated by the following examples

EXAMPLE 1

Fibres according to the invention in the form of a continuous yarn were prepared as follows: 800 ml of a 6% w/w dope was made by adding 28 g of carboxymethyl cellulose (ex Hercules), 12 g of alginate (ex Kelco), and 8 g of pectin (ex Aldrich Ltd) to 752 g of deionised water. The mixture was stirred with a high speed mixer until the ingredients had dissolved and the dope allowed to stand overnight to degas.

The degassed dope was then poured into a pressure vessel connected to the dope pumping/filtering system of a spinning rig. The pressure vessel was pressurised to 2 to 3 atmospheres with compressed air and the pump, 60 $\mu$m pore size filter and associated pipe work purged to remove any air bubbles. A 400 jet spinneret, previously ultrasonically cleaned for 20 minutes, was connected to the rig and the rig started. On exit from the spinneret, the dope was fed into a spin bath of 2 m length containing 30 L of 0.4 mol/dm3 of calcium chloride. The fibres so produced were threaded over three sets of rollers of a first godet and then over the rollers of a second godet. Propan-2-ol was dripped onto the fibres at a rate sufficient to wet the resulting yarn. The yarn was then passed into two baths, the first contained 4 L of propan-2-ol and the second contained 2.5 L of propan-2-ol. The propan-2-ol was maintained at a concentration to dry the yarn. The yarn was then passed through a set of pinch rollers that serve to apply tension to yarn. The yarn was then wound onto cones. The dope was supplied to the system at 6 ml per minute and a speed differential maintained between the first and second godets resulted in a stretch of 60%. The resulting yarn had a denier of 300 to 400.

EXAMPLE 2

A knitted wound dressing according to the invention was prepared comprising the yarn of example 1 and a crimped polyester yarn. The dressing was knitted on a crochet knitting machine (Model STP7 ex KOHLER) each needle of which creates a chain of interlocked loops (pillar or clain stitches). These form the warp threads of the dressing. The warp threads are held together by weft threads. 45 warp threads of stiches were knitted from 150 denier crimped polyester yarn. These were held together by 44 threads of the yarn of example 1 (in-laid yarn) to form a dressing.

EXAMPLE 3

A non-woven wound dressing according to the invention was made by mixing 200 g of the aborbent, composite fibres of example 1 cut into 5 cm lengths and 200 g of polypropylene staple fibre cut to 5 cm lengths in a rag roller to randomise the fibre. The mixture of fibres was then carded and cross-lapped into a web of 100 gsm basis weight. The web was then passed through heated callender rollers at 65° C. and pressure. The resultant product was slit into discrete dressings 10 cm by 10 cm square.

EXAMPLE 4

A staple yarn was made from the composite fibres of the invention in the following way. A mixture of the composite fibre (20 kg) and polypropylene (20 kg) (all 3 denier) was cut to a staple length of 40 mm and converted into a lap of approximately 100 gsm on a conventional short staple scutching line—a Truteschler Opening line. The line comprised a feed table, coarse fibre opener, volumetric feeder, fine opener and lap former.

The lap once formed was fed into a worsted type carding machine—a Thibeau CA6 comprising a weigh pan hopper, fibre opening section and a main carding cylinder. The web of fibres formed was condensed into the form of a sliver with an average weight of 5 grammes per metre length.

The slivers were then attenuated on a conventional short-staple draw frame—a Platts Globe Draw Frame—in which rollers operated at differential surface speeds to attenuate the multiple feed of slivers (6–8) into a uniform single sliver of uniform weight and thickness (approximately 3 g per metre length).

The drawn sliver was converted into roving on a roving frame which further attenuates the sliver. Twist was inserted to add cohesion to the strand. The roving was then spun on a ring spinning machine in which further drafting took place and twist was inserted to form the final yarn.

What is claimed is:

1. An absorbent, composite fibre comprising a matrix of from at least 10% to less than 50% by weight of water insoluble alginate having dispersed therein at least 40% by weight of another polysaccharide.

2. An absorbent composite fibre as claimed in claim 1 wherein the water insoluble alginate is calcium alginate.

3. An absorbent composite fibre as claimed in claim 1 wherein the other polysaccharide is selected from the group comprising carboxymethyl cellulose, carboxyethyl cellulose, other derivatives of cellulose, cellulose, pectin, hyaluronic acid, chitosan and mixture of these.

4. An absorbent composite fibre as claimed in claim 1 wherein the matrix comprises from 60% to 85% by weight of another polysaccharide.

5. An absorbent composite fibre as claimed in claim 4 wherein the matrix comprises from 70% to 80% by weight of another polysaccharide.

6. An absorbent, composite fibre as claimed in claim 3 wherein the other polysaccharide is carboxymethylcellulose, pectin or a mixture thereof.

7. An absorbent composite fibre as claimed in claim 1 wherein the matrix comprises from 10% to 49% by weight of the fibre of calcium alginate.

8. An absorbent, composite fibre as claimed in claim 7 wherein the matrix comprises from 20% to 30% by weight of the fibre of calcium alginate.

9. A method for making a composite, absorbent fibre comprising the following steps:
   (i) adding sodium alginate and another polysaccharide to water to form a dope;
   (ii) forcing the dope through a spinneret to form fibres;
   (iii) treating the resulting fibres with ions to convert the alginate to water insoluble alginate and cross-link the alginate to the other polysaccharide; and
   (iv) drying the fibres.

10. A method as claimed in claim 9 wherein the ions in step (iii) are calcium ions.

11. A wound dressing comprising an absorbent, composite fibre comprising a matrix of from 10% to less than 50% of water insoluble alginate having dispersed therein at least 40% of another polysaccharide.

12. A wound dressing comprising a mixture of discrete textile fibres and discrete absorbent, composite fibres wherein said absorbent, composite fibres comprise a matrix of from 10% to less than 50% of water insoluble alginate having dispersed therein at least 40% of another polysaccharide.

13. A wound dressing as claimed in claim 12 comprising from 50% by weight to 95% by weight of textile fibres and 5% by weight to 50% by weight of absorbent, composite fibres.

14. A wound dressing as claimed in claim 13 comprising from 75% to 90% by weight of textile fibres and 10% to 25% by weight of absorbent, composite fibres.

15. A wound dressing as claimed in claim 11 wherein the fibres are in the form of a woven fabric.

16. A wound dressing as claimed in claim 11 wherein the fibres are in the form of a carded web.

17. A method for treating a wound comprising placing a dressing as claimed in claim 11 in direct contact with the wound.

18. A wound dressing as claimed in claim 12 wherein the dressing is in the form of a knitted fabric comprising support yarn and in-laid yarn, the support yarn being substantially free of composite fibres.

19. A wound dressing as claimed in claim 18 wherein the fabric is a warp knitted fabric.

20. An absorbent, composite fibre as claimed in claim 7 wherein the matrix comprises from 30% to 40% by weight of the fibre of calcium alginate.

* * * * *